United States Patent
Mangual-Soto et al.

(10) Patent No.: US 11,931,587 B2
(45) Date of Patent: Mar. 19, 2024

(54) METHOD AND SYSTEM FOR IMPLANTING A SEPTAL WALL ELECTRODE

(71) Applicant: Pacesetter, Inc., Sylmar, CA (US)

(72) Inventors: Jan O. Mangual-Soto, Rho (IT); Wenwen Li, Studio City, CA (US); Yun Qiao, Sunnyvale, CA (US); Kyungmoo Ryu, Palmdale, CA (US)

(73) Assignee: PACESETTER, INC., Sylmar, CA (US)

( * ) Notice: Subject to any disclaimer, the term of this patent is extended or adjusted under 35 U.S.C. 154(b) by 200 days.

(21) Appl. No.: 17/367,855

(22) Filed: Jul. 6, 2021

(65) Prior Publication Data

US 2023/0008264 A1 Jan. 12, 2023

(51) Int. Cl.
*A61N 1/37* (2006.01)
*A61N 1/05* (2006.01)
*A61N 1/375* (2006.01)

(52) U.S. Cl.
CPC ........... *A61N 1/3702* (2013.01); *A61N 1/056* (2013.01); *A61N 1/3756* (2013.01)

(58) Field of Classification Search
None
See application file for complete search history.

(56) References Cited

U.S. PATENT DOCUMENTS

| | | | |
|---|---|---|---|
| 9,108,052 B2 * | 8/2015 | Jarrard | A61B 18/1206 |
| 11,045,653 B1 | 6/2021 | Makharinsky et al. | |
| 2011/0257696 A1 | 10/2011 | Holmstrom et al. | |
| 2020/0261725 A1 | 8/2020 | Yang et al. | |
| 2021/0015389 A1 | 1/2021 | Zhou et al. | |
| 2021/0106839 A1 | 4/2021 | Hine et al. | |

OTHER PUBLICATIONS

Extended European Search Report for corresponding EP Application No. 2216739 dated Sep. 23, 2022 (7 pages).

* cited by examiner

*Primary Examiner* — Catherine M Voorhees
*Assistant Examiner* — Elizabeth K So
(74) *Attorney, Agent, or Firm* — The Small Patent Law Group LLC; Josef L. Hoffmann

(57) ABSTRACT

A system is provided that includes a first electrode configured to be located within a septal wall, and a second electrode configured to be located outside of the septal wall. The system also includes an impedance circuit configured to measure impedance along an impedance monitoring (IM) vector between the first and second electrodes. One or more processors are also provided that are configured to obtain impedance data indicative of an impedance along the IM vector with the first electrode located at different depths within the septal wall, the impedance data including a set of data values associated with different depths of the first electrode within the septal wall. The one or more processors are also configured to determine when the first electrode is located at a target depth within the septal wall based on the impedance data.

20 Claims, 9 Drawing Sheets

METHOD AND SYSTEM FOR IMPLANTING A SEPTAL WALL ELECTRODE

FIELD OF THE INVENTION

Embodiments herein relate generally to implantable medical devices, and more particularly to the advancing of an electrode through a septal wall during implant.

BACKGROUND OF THE INVENTION

For some time right ventricular (RV) pacing has been utilized in patients with atrioventricular (AV) block. However, in certain instances, RV pacing has been shown to induce electrical and mechanical dyssynchrony. HIS bundle pacing (HBP) has been proposed as an alternative to RV pacing, taking advantage of physiological conduction, resulting in synchronous ventricle contraction. HBP has also been proposed as an alternative to biventricular cardiac resynchronization therapy (CRT) in patients with left bundle branch block (LBBB). Nevertheless, HBP still experiences challenges in identifying and targeting the HIS bundle, lead stability, and long-term pacing threshold.

A technique has been developed to directly capture left bundle branch (LBB) conduction by going deep into the ventricular septum. In particular, LBB pacing (LBBp) is clinically feasible in heart failure (HF) patients with LBBB and indication for cardiac resynchronization therapy (CRT). In particular, LBBp can potentially overcome limitations in HBP and offer a safer technique for conduction system pacing.

The location of the LBB, and thus target depth of an electrode at the distal tip of the lead is generally 1 to 1.5 cm distal along the septal wall of the HIS. During lead placement, the pacing lead is placed, or screwed into the myocardium on the right ventricle side and tunneled into the septum. This procedure is provided by a surgeon who has a limited ability to determine in real-time when the lead is located on the RV septum side wall, the middle on the intraventricular septum (e.g. mid-septum wall), and on the LV septum side wall. Placement of the lead such that the electrode at the distal tip of the lead is proximate the RBB in the septal wall is undesired and represents an unsuccessful implant. Additionally, advancing the lead too far through the LV septum side wall resulting in perforating the LV septum side wall into a left chamber of the heart is similarly undesired and problematic. Because the target depth proximate the LBB has a small range, greater accuracy in placement is desired.

SUMMARY

In accordance with embodiments herein, a system is provided that includes a first electrode configured to be located within a septal wall, and a second electrode configured to be located outside of the septal wall. The system also includes an impedance circuit configured to measure impedance along an impedance monitoring (IM) vector between the first and second electrodes, and a memory configured to store program instructions. One or more processors are also provided that, when executing the program instructions, are configured to obtain impedance data indicative of an impedance along the IM vector with the first electrode located at different depths within the septal wall, the impedance data including a set of data values associated with different depths of the first electrode within the septal wall. The one or more processors are also configured to determine when the first electrode is located at a target depth within the septal wall based on the impedance data.

Optionally, the target depth locates the first electrode proximate to the left bundle branch (LBB). In one aspect, the one or more processors are configured to determine that the first electrode is located proximate the LBB when the impedance data decreases from a first data value above a threshold to a second data value below the threshold. In another aspect, the one or more processors are configured to determine that the first electrode is located proximate the LBB based at least in part on a slope of the data value changes from positive to negative. In one example, the one or more processors are configured to determine that the first electrode is located proximate the LBB when the impedance data decreases from a first data value to a second data value at a rate greater than a rate threshold percentage. In another example, the determine operation includes determining when the data values satisfy a criteria of interest. Optionally, the determine operation further comprises comparing the data values, within the set of data values, to one another to determine a relation; and determining when the relation satisfies the criteria of interest.

Optionally, the criteria of interest is at least one of change in impedance value, a slope value, a change in impedance rate value, a change in impedance percentage, or a change in impedance rate percentage. In one aspect, the target depth includes a point where the first electrode is proximate the LBB and does not perforate a LV septum side wall distal wall of the septal wall. In another aspect, the system also includes a leadless IMD having the first electrode. In one example, the impedance data includes a septal wall component, a left ventricle or left atrial (LV/LA) chamber blood component, an outer heart wall component, and a secondary component for a region outside of the heart wall. In another example, the first electrode and the second electrode are configured to measure the impedance data, the first electrode provided proximate a distal tip of a lead located in the right ventricle RV, the second electrode located remote from the RV. In one embodiment, the second electrode is located on a housing of an implantable pulse generator, or in one of the right atrium, right ventricle, left ventricle, or left atrium.

In accordance with embodiments herein, a computer implemented method is provided wherein under control of one or more processors configured with specific executable instructions, the method includes obtaining impedance data indicative of an impedance along an impedance monitoring (IM) vector with a first electrode located at different depths within a septal wall, the impedance data including a set of data values associated with different depths of the first electrode within the septal wall. The method also includes determining when the first electrode is located at a target depth within the septal wall based on the impedance data.

Optionally, the method also includes determining that the first electrode is located proximate the LBB when the impedance data decreases from a first data value above a threshold to a second data value below the threshold. In one aspect, the method also includes determining that the first electrode is located proximate the LBB based at least in part on a slope of the data values changing from positive to negative. In yet another aspect, the determining operation includes determining when the data values satisfy a criteria of interest. In one example, the determining operation further comprises comparing the data values, within the set of data values, to one another to determine a relation; and determining when the relation satisfies the criteria of interest. In another example, obtaining the impedance data comprises measuring the impedance data with the first electrode and the second electrode, the first electrode provided proximate a distal tip of a lead located in the right ventricle RV, the second electrode located remote from the RV. In one embodiment, the method also includes determining that the first electrode is located proximate the LBB when the impedance data decreases from a first data value to a second data value at a rate greater than a rate threshold percentage.

DETAILED DESCRIPTION

Figure 1:
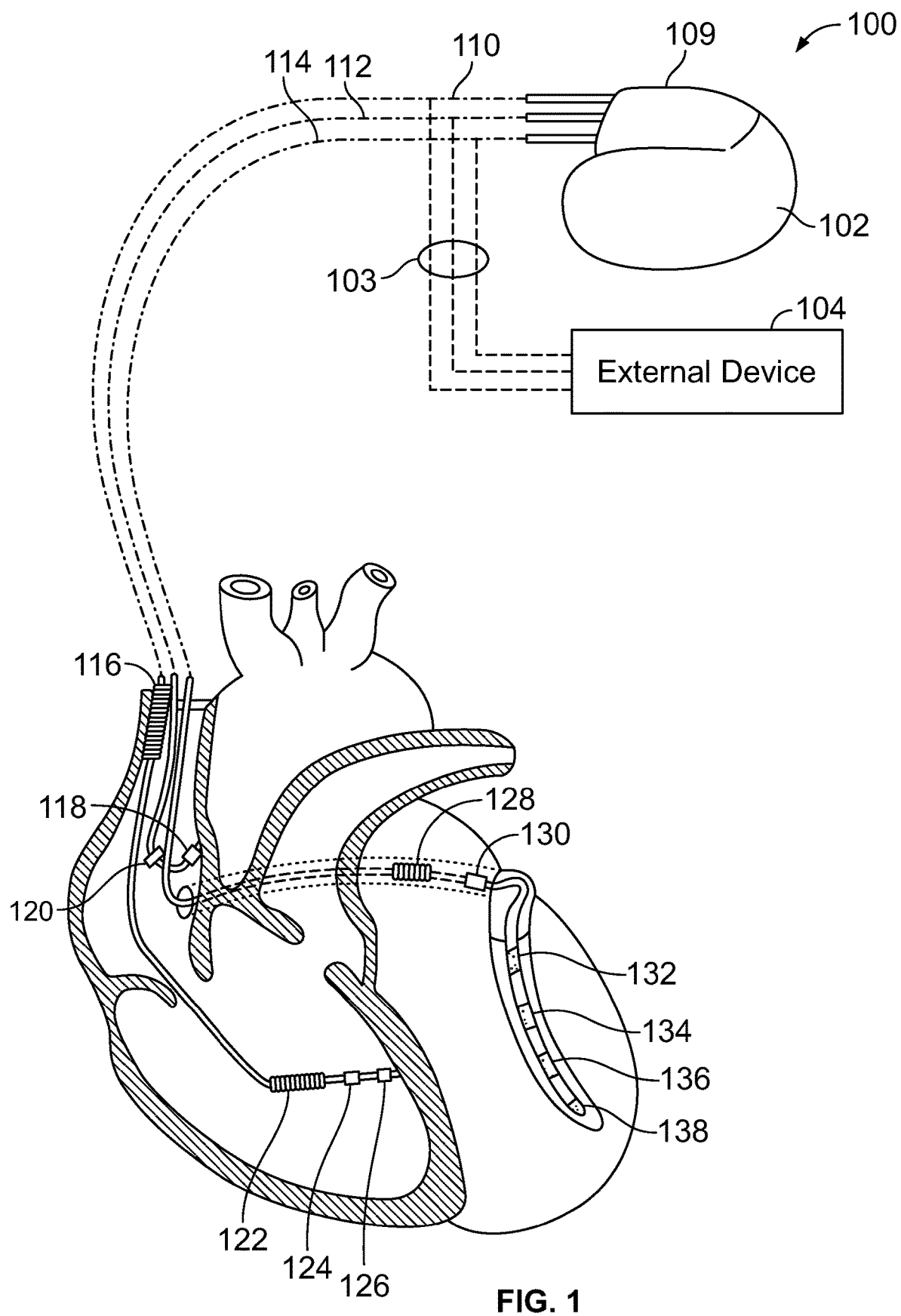
FIG. 1 illustrates an implantable medical device (IMD) intended for subcutaneous implantation at a site near the heart in accordance with embodiments herein.

Embodiments set forth herein include methods and systems for continuous monitoring of lead impedance during the fixation, or tunneling, into the septal wall. The lead impedance can provide a profile, or set of data values, related to the depth the lead into the septal wall. Taking advantage of this information, a determination is made when a first electrode has reached the mid-septum wall and passed onto the LV septum side wall.

The impedance along an impedance monitoring (IM) vector is measured between a first electrode at a distal tip of the lead and a second electrode located remote from the first electrode. Optionally, the first electrode is placed on a leadless device, but similarly tunneled for placement proximate an LBB. The impedance is recorded for the start of lead fixation, on the RV septum side ($\Omega_i$). As the first electrode is advanced into the septal wall, new measurements of the impedance are recorded ($\Omega_t$) to provide the set of data values. The set of data values can include beat to beat values, an average of several beats, etc. Based on the set of data values related to the impedance, $\Omega_t$, a determination is made when the first electrode has been advanced to a target depth proximate the LBB. As used herein, the first electrode is considered proximate an LBB when any portion or surface of the first electrode engages the left ventricle (LV) septum side wall of the septal wall or can obtain measurements or provide treatment related to the LV septum side wall.

In one example, the impedance $\Omega_t$, can be compared to the previous recorded measurement, $\Omega_{t-1}$. If the impedance $\Omega_t$ is greater than the previous measurement, $\Omega_{t-1}$, or the change in impedance is greater than 0, then an indication is provided that the first electrode is still on the RV septum side of the septal wall. In particular, the impedance is increasing, and additional sets of data values are obtained. Alternatively, when the measured impedance is less than the previous recorded impedance measurement, then a maximum impedance value has been reached, indicative that the first electrode has passed the mid septal line and is tunneling into the LV septum side of the septal wall.

Upon reaching the mid septal line, the impedance data is continuously reviewed for a determination that the first electrode is proximate the LBB, and to prevent perforation into a left chamber of the heart. In one example, when the current measured impedance ($\Omega_t$) is within a given range of the initial recorded impedance ($\Omega_i$), the desired target depth is determined to have been reached. In other examples, embodiments may determine that the first electrode is proximate the LBB in the septal wall based on a measured impedance decrease from the maximum impedance value, a rate threshold decrease, a rate threshold percentage decrease, etc. Once a determination is made the first electrode is proximate the LBB, a message may be provided to the clinician to stop further tunneling.

Embodiments may be implemented in connection with one or more implantable medical devices (IMDs). Non-limiting examples of IMDs include one or more of implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker, and the like.

Additionally or alternatively, the IMD may be a leadless implantable medical device (LIMD) that is directly screwed or otherwise secured to the septal wall with a distal electrode implanted at a target depth within the septal wall. The leadless IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the leadless IMD may communicate and coordinate monitoring and/or therapy delivery with a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, the IMD may utilize one or more structural and/or functional aspects of the device(s) described in U.S. Patent Application having Docket No. A15E1059, U.S. patent application Ser. No. 15/084,373, filed Mar. 29, 2016, entitled, "METHOD AND SYSTEM TO DISCRIMINATE RHYTHM PATTERNS IN CARDIAC ACTIVITY," which is expressly incorporated herein by reference.

Embodiments may be implemented in connection with one or more passive IMDs (PIMDs). Non-limiting examples of PIMDs may include passive wireless sensors used by themselves, or incorporated into or used in conjunction with other implantable medical devices (IMDs) such as cardiac monitoring devices, pacemakers, cardioverters, cardiac rhythm management devices, defibrillators, neurostimulators, leadless monitoring devices, leadless pacemakers, replacement valves, shunts, grafts, drug elution devices, blood glucose monitoring systems, orthopedic implants, and the like. For example, the IMD with an electrode implanted in the septal wall may operate in combination with monitoring additional characteristics such as described in U.S. Pat. No. 9,265,428 entitled "Implantable Wireless Sensor", U.S. Pat. No. 8,278,941 entitled "Strain Monitoring System and Apparatus", U.S. Pat. No. 8,026,729 entitled "System and Apparatus for In-Vivo Assessment of Relative Position of an Implant", U.S. Pat. No. 8,870,787 entitled "Ventricular Shunt System and Method", and U.S. Pat. No. 9,653,926 entitled "Physical Property Sensor with Active Electronic Circuit and Wireless Power and Data Transmission", which are all hereby incorporated by reference in their respective entireties.

All references, including publications, patent applications and patents, cited herein are hereby incorporated by reference to the same extent as if each reference were individually and specifically indicated to be incorporated by reference and were set forth in its entirety herein.

I. Terms and Abbreviations

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g, left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The terms "beat", and "cardiac event" are used interchangeably and refer to both normal or abnormal events.

The terms "impedance monitoring vector" and "IM vector" as used interchangeably herein refers to a straight path between a first electrode and a second electrode where impedance measurements are obtained. The IM vector continuously changes in real-time as a first electrode is advanced through a septal wall because the distance between the first electrode and second electrode continues to change. The impedance measurement obtained includes all portions, including septal wall, fluids and blood, outer heart wall, and secondary components between the first electrode and second electrode.

The term "target depth" as used herein may be utilized to describe all depths that place a first electrode proximate a region of interest within the heart's conductive pathways (e.g., the RBB, LBB, Purkinje fibers, etc.) without penetrating the distal end wall of the corresponding chamber. For example, the target depth may include a range of depth through the septal wall, starting with the depth when a first electrode engages the LV septum side of the septal wall to a depth right before the distal end wall proximate the LBB is perforated by the first electrode. The term "depth", alone, refers to how far into the heart wall (e.g., septal wall) that the first electrode has advanced, whereas the target depth is a desired location of where the first electrode is to be implanted. The target depth in one example may be measured in centimeters (cm), and in one embodiment is in a range between 1 to 1.5 cm into a septal wall.

The term "criteria of interest" when used herein shall mean any and all parameters, characteristics, measurements, settings, rates, percentages, thresholds, etc. that may be utilized to determine the depth of an electrode within a septal wall of the heart. Optionally, criteria of interest can be detected, calculated, obtained, determined, or the like. Example criteria of interest can include, a threshold of an impedance parameter, a length of time, a rate threshold, a threshold Ohm data value, the direction of slope of a data value of the change in impedance, the number of times an impedance value is obtained, an average of a previous number of impedance measurements, a mode, medium, other mathematical relationship, mathematical model, function, algorithm, or the like related to a parameter, characteristic, measurement, setting, rate, percentage, threshold, etc.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "obtains" and "obtaining", as used in connection with data, signals, information, and the like, include at least one of i) accessing memory of an external device or remote server where the data, signals, information, etc. are stored, ii) receiving the data, signals, information, etc. over a wireless communications link between the IMD and a local external device, and/or iii) receiving the data, signals, information, etc. at a remote server over a network connection. The obtaining operation, when from the perspective of an IMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The term "real-time" refers to a time frame contemporaneous with a normal or abnormal episode occurrence. For example, a real-time process or operation would occur during or immediately after (e.g., within minutes or seconds after) a cardiac event, a series of cardiac events, an arrhythmia episode, and the like.

II. System Overview

FIG. 1 illustrates an IMD 100 that in one example is a dual-chamber stimulation device capable of treating arrhythmias with stimulation therapy, including cardioversion, defibrillation, anti-tachycardia pacing, HF pacing, and pacing stimulation, as well as capable of detecting heart failure, evaluating its severity, tracking the progression thereof, and controlling the delivery of therapy and warnings in response thereto.

In the example of FIG. 1, the IMD 100 includes a housing 102 that is joined to a header assembly 109 that holds receptacle connectors connected to a right ventricular lead 110, a right atrial lead 112, and a coronary sinus lead 114, respectively. The leads 112, 114 and 110 measure cardiac signals of the heart. While the present embodiment is described in connection with CA signals and heart conditions, it is understood that embodiments may be implemented in connection with other types of biological signals and other types of physiologic and non-physiologic conditions. Additionally, in other example embodiments, a lead may be implanted into a septal wall.

The right atrial lead 112 includes an atrial tip electrode 118 and an atrial ring electrode 120. The coronary sinus lead 114 includes a left atrial ring electrode 128, a left atrial coil electrode 130 and one or more left ventricular electrodes 132-138 (e.g., also referred to as P1, M1, M2 and D1) to form a multi-pole LV electrode combination. The right ventricular lead 110 includes an RV tip electrode 126, an RV ring electrode 124, an RV coil electrode 122, and an SVC coil electrode 116. The leads 112, 114 and 110 detect IEGM signals that are processed and analyzed as described herein. The leads 112, 114 and 110 also delivery therapies as described herein.

During implantation, an external device 104 is connected to one or more of the leads 112, 114 and 110 through temporary inputs 103. The inputs 103 of the external device 104 receive IEGM signals from the leads 112, 114 and 110 during implantation and display the IEGM signals to the physician on a display. Hence, the external device 104 receives the IEGM cardiac signals through telemetry circuit inputs. The physician or another user controls operation of the external device 104 through a user interface. While the example embodiment of FIG. 1 illustrates an IMD 100 that includes leads, such embodiment is for exemplary purposes only, in other example embodiments, the IMD may be a leadless IMD.

Embodiments may utilize one or more leadless IMD that are implanted at various locations within the heart, such as in the RA, RV, LA, LV. A leadless IMD may be implanted in at an RV apical septum where the target depth represents a depth within the apical septum at which the conductive pathway is located (e.g., the RBB, Purkinje fibers). Additionally or alternatively, a leadless IMD may be implanted in at an LV apical septum where the target depth represents a depth within the apical septum at which the conductive pathway is located (e.g., the LBB, Purkinje fibers).

Figure 2:
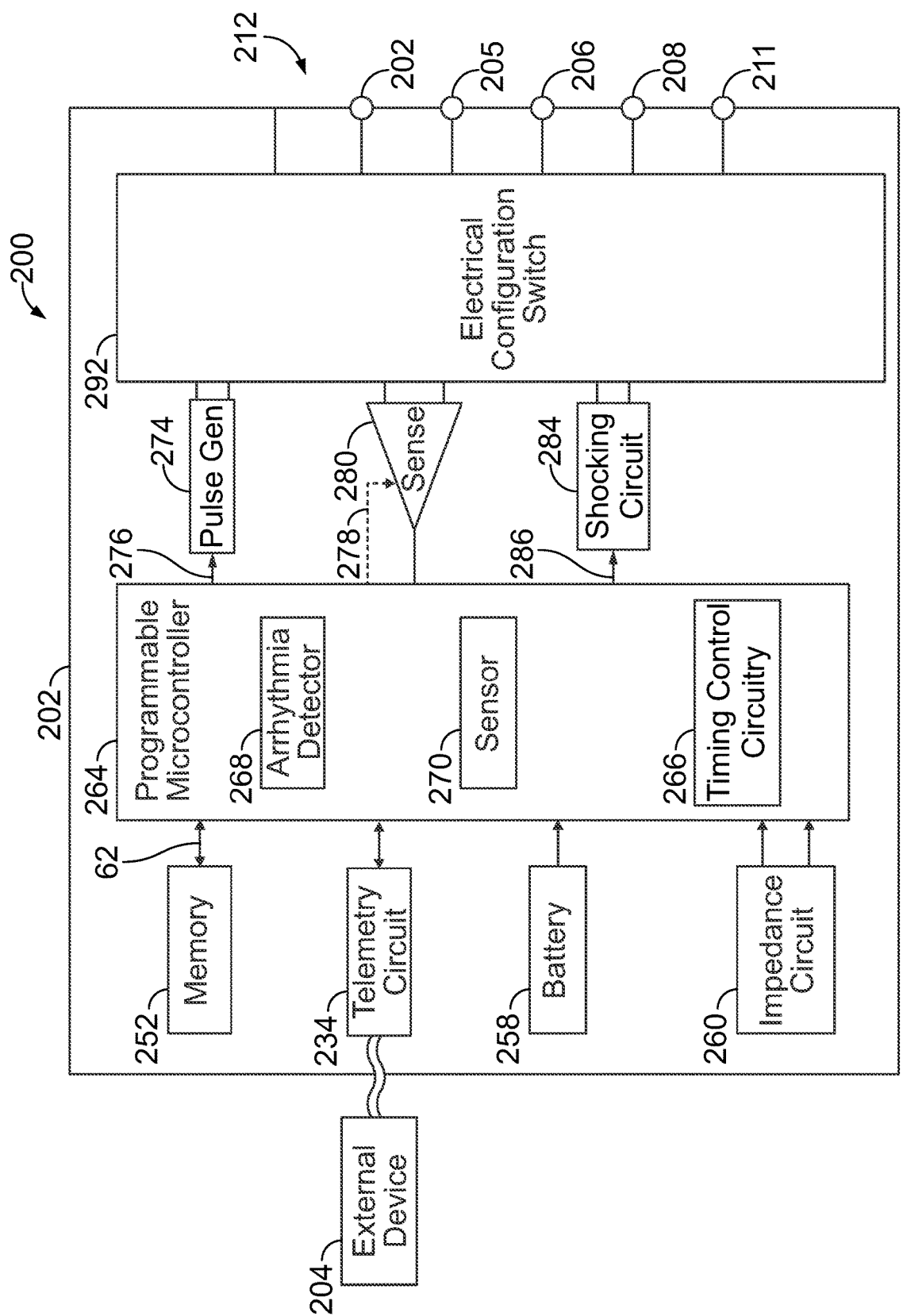
FIG. 2 illustrates a block diagram of an IMD in accordance with embodiments herein.

FIG. 2 illustrates an example block diagram of a IMD 200 that is implanted into the patient as part of the implantable cardiac system. While described as an implantable cardiac system, this is for exemplary purposes only, and other IMDs are contemplated. In this embodiment, the IMD 200 may be implemented as a full-function biventricular pacemaker, equipped with both atrial and ventricular sensing, and pacing circuitry for four chamber sensing and stimulation therapy (including both pacing and shock treatment). The pacing circuitry in one example includes HF pacing. Optionally, the IMD 200 may provide full-function cardiac resynchronization therapy. Alternatively, the IMD 200 may be implemented with a reduced set of functions and components. For instance, the monitoring device may be implemented without ventricular sensing and pacing.

The IMD 200 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals 202, 205, 206, 208, and 211 for electrodes 212. The type and location of each electrode may vary. For example, the electrodes may include various combinations of ring, tip, coil and shocking electrodes and the like.

The IMD 200 also includes a telemetry circuit 234 that as a primary function allows intracardiac electrograms and status information relating to the operation of the IMD 200 (as contained in the microcontroller 264 or memory 252) to be sent to the external device 204 through the established communication link 250. Specifically, the telemetry circuit wirelessly communicates with at least one of the external device 204 or second implanted device.

The IMD 200 also includes a programmable microcontroller 264 that controls various operations of the IMD 200. Microcontroller 264 includes a microprocessor (or equivalent control circuitry), RAM and/or ROM memory, logic and timing circuitry, state machine circuitry, and I/O circuitry. The IMD 200 further includes a first chamber pulse generator 274 that generates stimulation pulses for delivery by one or more electrodes coupled thereto. The pulse generator 274 is controlled by the microcontroller 264 via control signal 276. The pulse generator 274 is coupled to the select electrode(s) via an electrode configuration switch 292, which includes multiple switches for connecting the desired electrodes to the appropriate I/O circuits, thereby facilitating electrode programmability. The switch 292 is controlled by a control signal 286 from the microcontroller 264.

Microcontroller 264 is illustrated to include timing control circuitry 266 to control the timing of the stimulation pulses (e.g., pacing rate, atrio-ventricular (AV) delay, atrial interconduction (A-A) delay, or ventricular interconduction (V-V) delay, etc.). Microcontroller 264 also has an arrhythmia detector 268 for detecting arrhythmia conditions. Although not shown, the microcontroller 264 may further include other dedicated circuitry and/or firmware/software components that assist in monitoring various medical conditions, including of the patient's heart and managing pacing therapies, including HF pacing.

The IMD 200 also includes one or more sensors 270. The one or more sensors 270 can include physiological sensors that detect characteristics associated with the heart of the patient. Alternatively, the one or more sensors 270 can be environmental sensors that detect characteristics associated with the environment of the patient. In one example, the sensor 270 is an accelerometer that obtains location information with respect to gravitational force while the IMD 200 collects cardiac activity signals in connection with multiple cardiac beats. The microcontroller 264 may utilize the signals from the accelerometer to determine a change in posture, change in activity, or the like. While the sensor 270 shown as being included within the housing 202, the sensor 270 may be external to the housing 202, yet still, be implanted within or carried by the patient.

The IMD 200 is further equipped with a communication modem (modulator/demodulator) to enable wireless communication with other devices, implanted devices, and/or external devices. The IMD 200 also includes sensing circuitry 280 selectively coupled to one or more electrodes that perform sensing operations, through the switch 292, to detect the presence of cardiac activity.

The output of the sensing circuitry 280 is connected to the microcontroller 264 which, in turn, triggers or inhibits the pulse generator 274 in response to the absence or presence of cardiac activity. The sensing circuitry 280 receives a control signal 278 from the microcontroller 264 for purposes of controlling the gain, threshold, polarization charge removal circuitry (not shown), and the timing of any blocking circuitry (not shown) coupled to the inputs of the sensing circuitry.

The microcontroller 264 is also coupled to a memory 252 by a suitable data/address bus 262. The programmable operating parameters used by the microcontroller 264 are stored in memory 252 and used to customize the operation of the IMD 200 to suit the needs of a particular patient. Such operating parameters define, for example, pacing pulse amplitude, pulse duration, electrode polarity, rate, sensitivity, automatic features, HF pacing features, arrhythmia detection criteria, and the amplitude, waveshape and vector of each shocking pulse to be delivered to the patient's heart within each respective tier of therapy. Such shocking pulse can be an LV shock, MV shock, HV shock, etc.

A battery 258 provides operating power to all of the components in the IMD 200. The IMD 200 further includes an impedance circuit 260, which can be used for many things, including: lead impedance surveillance during the acute and chronic phases for proper lead positioning or dislodgement; detecting operable electrodes and automatically switching to an operable pair if dislodgement occurs; measuring thoracic impedance for determining shock thresholds; detecting when the device has been implanted; measuring stroke volume; and detecting the opening of heart valves; and so forth. In one example the impedance circuit is considered an impedance measuring circuit. The impedance circuit 260 is coupled to the switch 292 so that any desired electrode may be used. In one example, the impedance circuit 260 can be utilized during implant to assist in locating an electrode. The IMD 200 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 264 further controls a shocking circuit 284 by way of a control signal 286, including for LV shocks, MV shocks, HV shocks, etc.

The physiologic sensor may be implemented as an accelerometer and may be implemented utilizing all or portions of the structural and/or functional aspects of the methods and systems described in U.S. Pat. No. 6,937,900, titled "AC/DC Multi-Axis Accelerometer for Determining A Patient Activity and Body Position;" U.S. application Ser. No. 17/192,961, filed Mar. 5, 2021, (Attorney docket 13-0397US1) (client docket 13967US01), titled "SYSTEM FOR VERIFYING A PATHOLOGIC EPISODE USING AN ACCELEROMETER"; U.S. application Ser. No. 16/869,733, filed May 8, 2020, (Attorney docket 13-0396US1) (client docket 13964US01), titled "METHOD AND DEVICE FOR DETECTING RESPIRATION ANOMALY FROM LOW FREQUENCY COMPONENT OF ELECTRICAL CARDIAC ACTIVITY SIGNALS;" U.S. application Ser. No. 17/194,354, filed Mar. 8, 2021, (Attorney docket 13-0395US1) (client docket 13949US01), titled "METHOD AND SYSTEMS FOR HEART CONDITION DETECTION USING AN ACCELEROMETER," the complete subject matter which is expressly incorporated herein by reference.

Figure 3:
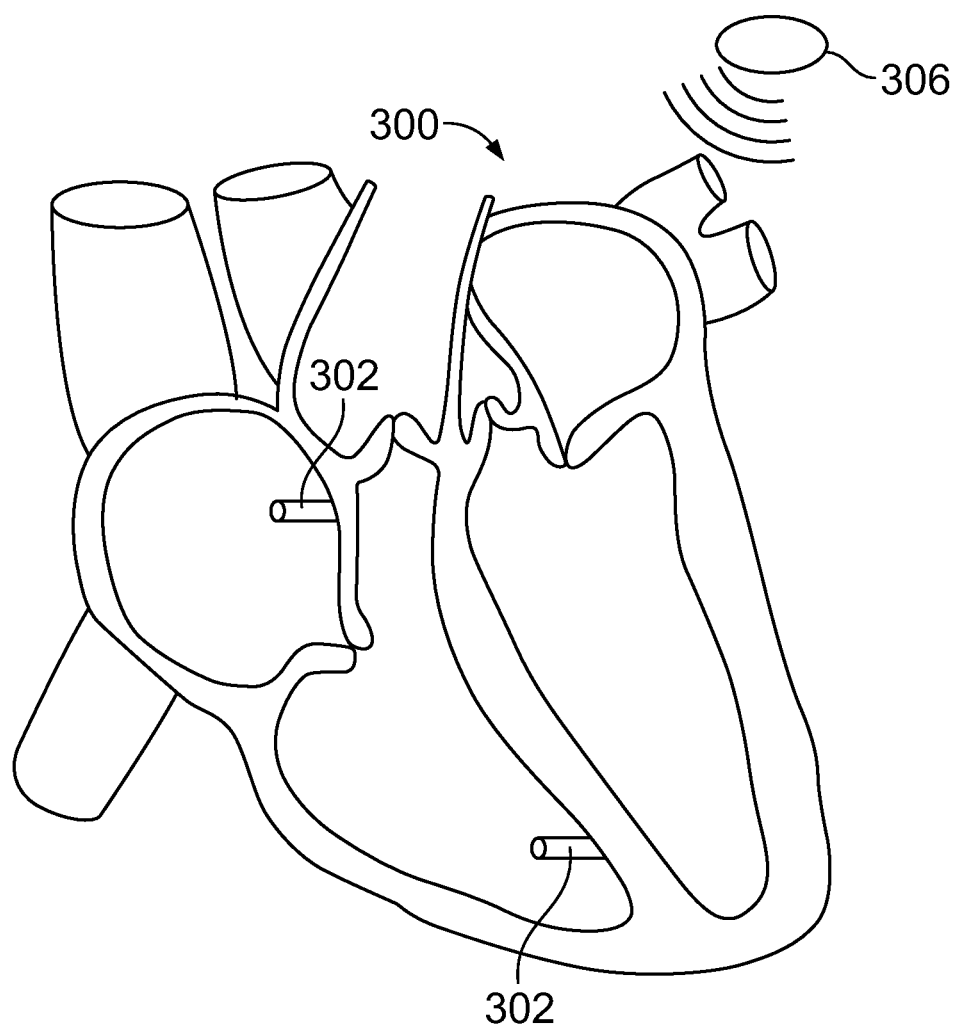
FIG. 3 illustrates an IMD intended for implantation in the heart in accordance with embodiments herein.

FIG. 3 illustrates a pictorial view depicting an embodiment of an implantable system 300 that may be utilized to deliver various types of therapy and/or monitor physiologic conditions in accordance with embodiments herein. The system 300 comprises one or more implantable medical devices (IMD) 302. As described further below, the IMD 302 comprises a housing, multiple electrodes coupled to the housing, and a pulse generator hermetically contained within the housing and electrically coupled to the electrodes. The pulse generator may be configured for sourcing energy internal to the housing, generating, and delivering electrical pulses to the electrodes. A controller can also be hermetically contained within the housing as part of the pulse generator and communicatively coupled to the electrodes. The controller can control, among other things, recording of physiologic characteristics of interest and/or electrical pulse delivery based on the sensed activity.

In the example of FIG. 3, a pair of IMDs 302 are illustrated to be located in different first and second chambers of the heart. For example, one IMD 302 is located in the right atrium (RA), while a second IMD 302 is located in the right ventricle (RV). Optionally, the IMD 302 located in the RA is advanced to a target depth to locate a distal, or first electrode, at the HIS or AV node. In one example, the IMD 302 is advanced by screwing the IMD 302 to the target depth. Alternatively, in another example, the IMD 302 located in the RV can be advanced, screwed, etc. to a target depth with the distal, or first electrode at one of the RBB, or LBB.

The IMDs 302 coordinate the operation therebetween based in part on information conveyed between the IMDs 302 during operation. The information conveyed between the IMDs 302 may include, among other things, physiologic data regarding activity occurring in the corresponding local chamber. For example, the atrial IMD 302 may perform sensing and pacing operations in the right atrium, while the ventricular IMD 302 may perform sensing and pacing operations in the right ventricle. The physiologic data conveyed between the atrial and ventricular IMDs 302 includes, among other things, the detection of sensed intrinsic local events (e.g. sensed atrial events or sensed ventricular events). The physiologic data also includes paced local events (e.g. paced atrial events or paced ventricular events).

Additionally or alternatively, the information conveyed between the atrial and ventricular IMDs 302 may include device related information, such as synchronization information, oscillator clock timing information, battery status, quality information regarding received signals and the like. Additionally or alternatively, the physiologic data may include other information.

While the IMDs 302 are located in the right atrium and ventricle, optionally, the IMDs 302 may be located in other chamber combinations of the heart, as well as outside of the heart. Optionally, the IMDs 302 may be located in a blood pool without directly engaging local tissue. Optionally, the IMDs 302 may be implemented solely to perform monitoring operations, without delivery of therapy. For example, an IMD 302 may be a cardiac monitoring device that is located outside of, but in relatively close proximity to, the heart. As another example, one or more IMDs 302 may represent a subcutaneous implantable device located in a subcutaneous pocket and configured to perform monitoring and/or deliver therapy. As another example, one or more IMDs 302 may be configured to perform neural stimulation. The IMD 302 is located proximate to nerve tissue of interest (e.g., along the spinal column, dorsal root, brainstem, within the brain, etc.). The IMD 302 may be configured to perform monitoring of neural activity, without delivering neural stimulation. Optionally, the IMD 302 may not require tissue contact to monitor and/or deliver therapy. For example, blood pressure may be measured with or without direct tissue contact. The IMDs 302 may also receive communication, data, information, signals, etc. from an external device 306.

In the example of FIG. 3, the IMDs 302 represent leadless devices in which the electrodes are located directly on the housing of the device, without a lead extending from the device housing. Optionally, the IMDs 302 may be implemented with leads, where the conducted communication occurs between one or more electrodes on the lead and/or on the housing. Examples of other IMDs that may be configured to implement the conducted communication embodiments described herein are described in U.S. Pat. No. 9,168,383, issued Oct. 27, 2015, and titled "LEADLESS CARDIAC PACEMAKER WITH CONDUCTED COMMUNICATION," the complete subject matter of which is incorporated by reference in its entirety.

Figure 4A:
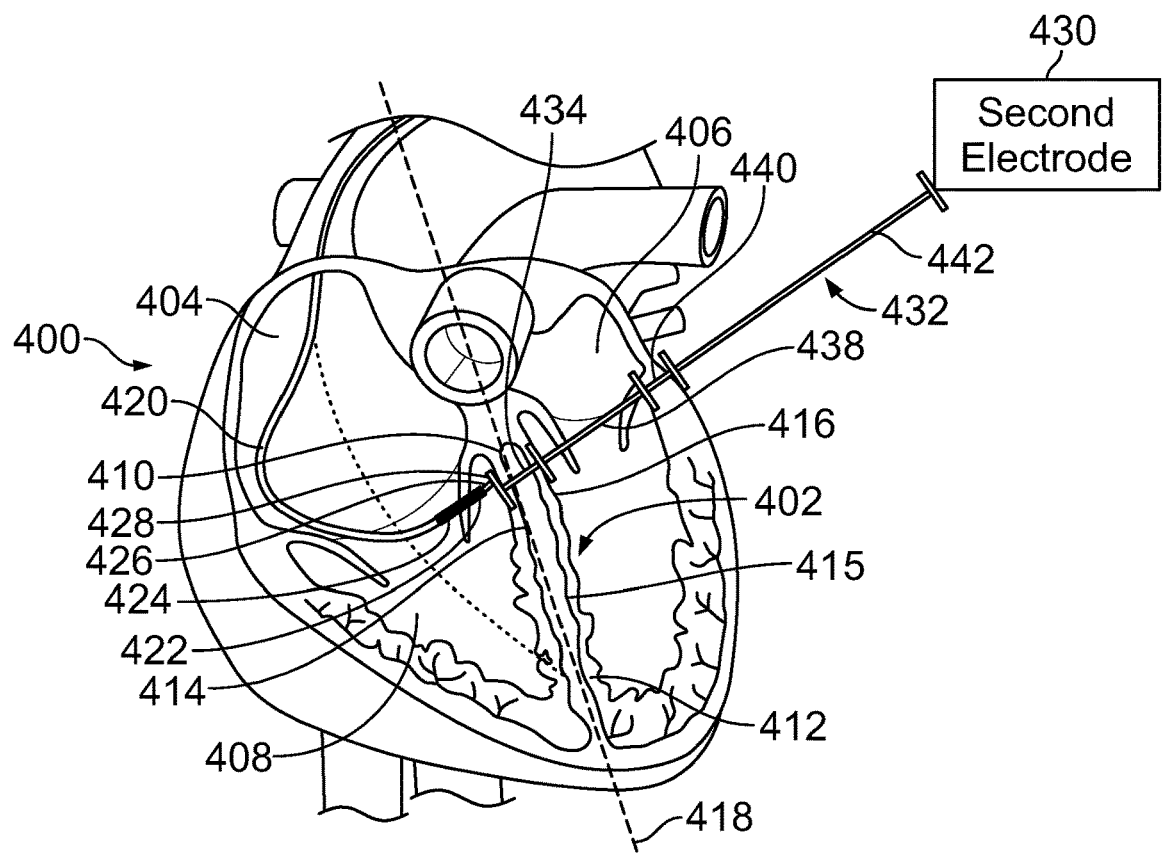
FIG. 4A illustrates a schematic diagram of an electrode at a first position being implanted into a heart, in accordance with embodiments herein.
Figure 4B:
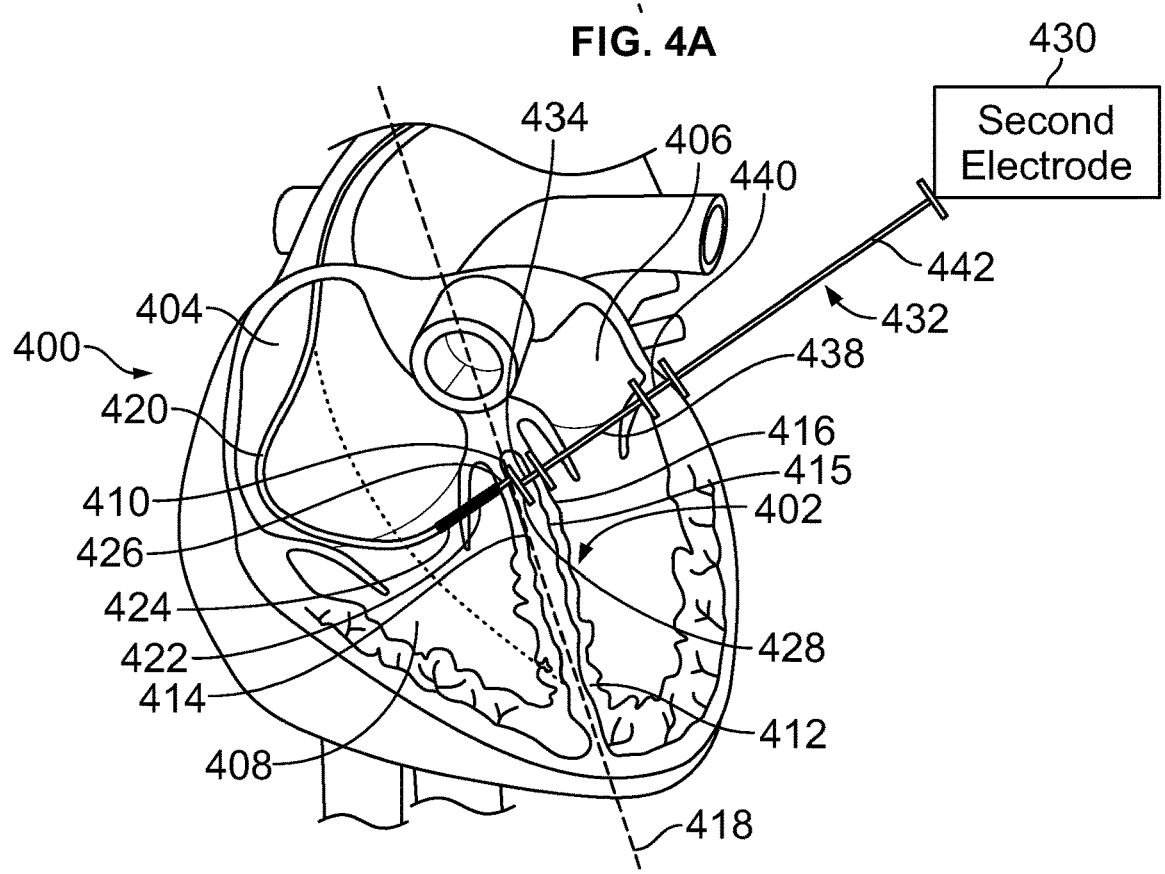
FIG. 4B illustrates a schematic diagram of an electrode at a second position being implanted into a heart, in accordance with embodiments herein.
Figure 4C:
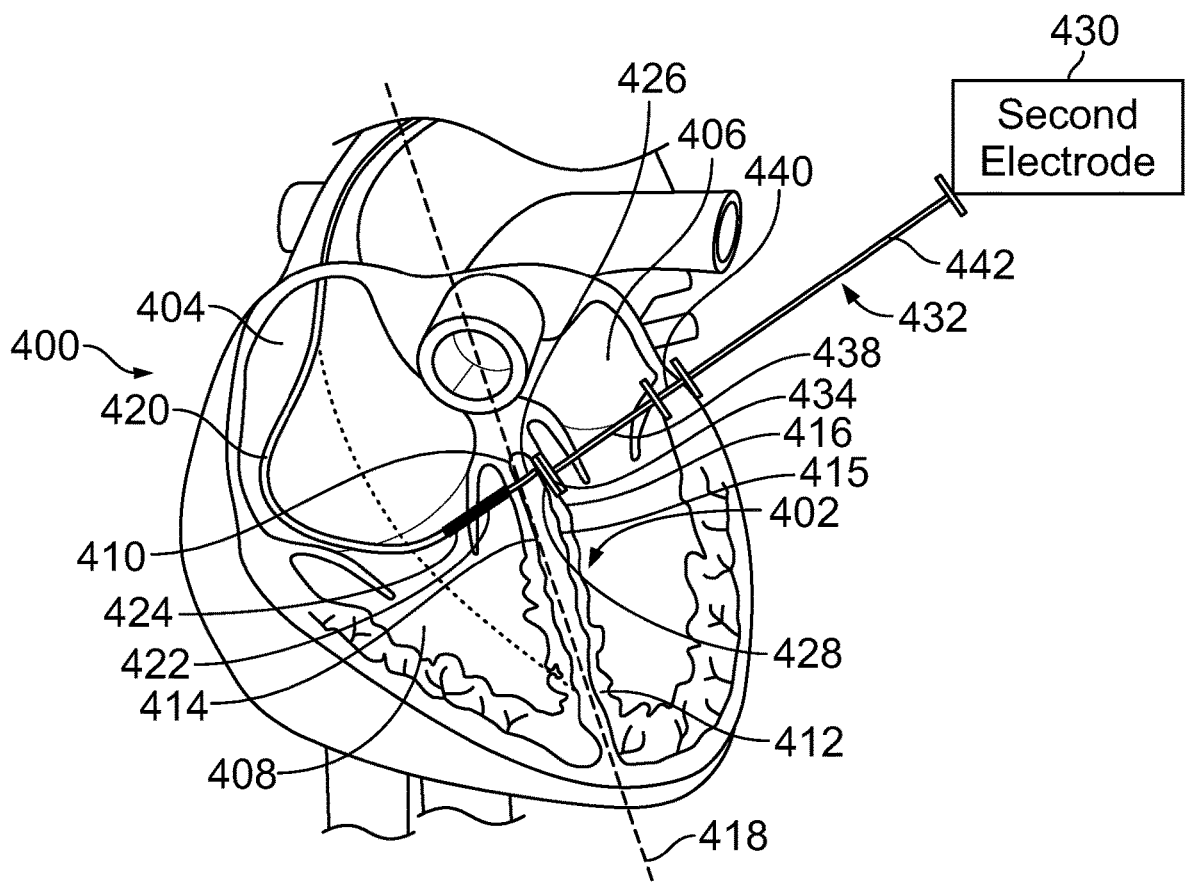
FIG. 4C illustrates a schematic diagram of an electrode at a third position being implanted into a heart, in accordance with embodiments herein.

FIGS. 4A-4C illustrate the advancement of a lead into a heart 400 for placement of an electrode in and through a septal wall 402 in real-time. The heart 400 includes a right atrium 404, left atrium 406, left ventricle 408, and right ventricle with the septal wall 402 centrally located extending from a HIS 410 to an apex 412 and separating the right chambers of the heart 400 from the left chambers of the heart 400. The septal wall 402 includes a RV septum side wall 414 on the right side of a mid-septum wall 415, and a LV septum side wall 416 on the left side of the mid-septum wall 415. A mid septal line 418 extends through the mid-septum wall 415 and represents the midway line through the septal wall 402.

In the example embodiment of FIGS. 4A-4C, a catheter 420 is illustrated that includes a lead 422 of an IMD that extends from a proximal end 424 to a distal end 426. The lead 422 includes a first electrode 428 at a point at the distal end 426 of the lead. While a lead 422 is illustrated, in other example embodiments, a leadless IMD can similarly be inserted and advanced through the septal wall 402. Additionally, while in the example embodiment, the process and methodology are utilized to determine a depth of the first electrode during advancement of a first electrode 428 into a septal wall 402, in other example embodiments, the process and methodology is utilized to determine the depth of a first electrode through a different portion of the heart. In one example, the process and method are utilized to determine the depth of a first electrode proximate an outer chamber wall, including implanting of a leadless device in an outer chamber wall, apical septum, and the like.

A second electrode 430 is provided remote of the first electrode, forming an IM vector 432 between the first electrode 428 and second electrode 430. In one example, the second electrode 430 is subcutaneously placed within the patient. Optionally, the second electrode 430 is placed on the housing of an IMD such as an implantable cardioverter-defibrillator (ICD) or an implantable cardiac monitor (ICM). In another example, the second electrode is not subcutaneous and instead is placed on a patient's body. In each instance, an impedance between the first electrode 428 and second electrode 430 along the IM vector 432 can be measured to provide impedance data in real-time. In one example the impedance data is a measurement provided in ohms. The location of the second electrode 430 can vary depending on the patient, the IMD in use, etc. Still, for each patient, during insertion of the first electrode into the heart, the second electrode 430 is always in the same location. In this manner, the only variable that varies the impedance between the first electrode 428 and second electrode 430 is the depth of the first electrode through a portion of the heart, that in one example can include the RV septum side wall 414, mid-septum wall 415, and LV septum side wall 416.

Each of the FIGS. 4A-4C illustrate a different insertion depth of the distal end 426 of the lead 422 into the septal wall 402. As the first electrode 428 advances into the RV septum side wall 414, through the mid-septum wall 415 and to the LV septum side wall 416 proximate the LBB, the consistency of the medium through which the impedance data is obtained between the first electrode 428 and second electrode 430 continuously changes. As an example, in FIG. 4A, the first electrode is in a first position and engages the RV septum side wall 414 such that the impedance data related to the IM vector includes a septal wall component 434, an LV and/or LA (LV/LA) chamber blood component 438, an outer heart wall component 440, and a secondary component 442 for a region outside of the heart wall.

The septal wall component 434 includes a proximal portion of the RV septum side wall 414 and extends to a distal portion of the LV septum side wall 416. The LV/LA chamber blood component 442 is representative of the blood flowing through either one of or both the left ventricle and left atrial. As an example, depending on the location of the second electrode 430, the IM vector 432 between the first electrode 428 and second electrode 430 can pass through only the LV, only the LA, or through both the LV and LA. In this manner, the impedance data may include an LV and/or LA component. The outer heart wall component 440 includes the outer wall of the heart, while the secondary component 442 includes all other body tissues, fluids, bones, etc. located outside of the heart and along the IM vector 432 between the first electrode 428 and second electrode 430. Optionally, the second electrode may be placed at different locations, varying the medium through which the IM vector 432 traverses. Still, once the second electrode 430 is placed, the impedance caused by each component does not vary. In this manner, as the first electrode is advanced through different components, the change in impedance is directly related to the distance between the first electrode and second electrode resulting in a determination of the depth of the first electrode.

FIG. 4A illustrates the lead in a first position when the electrode is first engaging the RV septum side wall 414, and is not proximate the LV septum side wall 416. At this location, the impedance data includes all of the components, including the entire septal wall component 434, LV/LA chamber blood component 438, outer heart wall component 440, and the secondary component 442. In particular, the IM vector 432 is at the greatest length and distance between the first electrode 428 and second electrode 430.

FIG. 4B illustrates the lead in a second position after the lead has been advanced through the RV septum side wall 414 into the mid-septum wall 415, but is still not proximate the LV septum side wall 416. In one example, the lead is pushed through the RV septum side wall 414. Alternatively, the lead is rotated, or screwed through the RV septum side wall. At the second position, the electrode engages the mid-septum wall 415, and the septal wall component 434 is varied as a result of no long having the RV septum side wall affecting the impedance value. As a result, the impedance measurement only extends through part of the septal wall component 434, the LV/LA chamber blood component 438, the outer heart wall component 440, and the secondary component 442. In one example, the impedance increases as the first electrode 428 advances toward the mid-septum wall 415 through the RV septum side wall 414. In another example, the impedance from the first position illustrated in FIG. 4A to the second position illustrated in FIG. 4B increases from 600 Ohms to 725 Ohms. In another example, the impedance increases by at least 100 Ohms. In yet another example, the impedance increases in a range between 100-150 Ohms. In particular, the impedance values are dependent on the patient, so while in one example the initial impedance may be 600 Ohms for one patient with a range between 100-150 Ohms, the initial value may be 500 Ohms with a range of 150-200 Ohms for another patient. Still, for each patient, the impedance reaches a maximum value in the mid-septum wall 415, and a decrease in impedance after an increase is indicative the LV septum side wall 416 is being approached.

FIG. 4C illustrates the lead in a third position after the lead has been advanced through a distal portion of the mid-septum wall 415 and the first electrode 428 is proximate the LBB. The third position represents the desired location of the lead 422 and first electrode 428 for providing therapy. Consequently, during the implant, the clinician desires to stop advancing the lead 422 at this location. In the third position, both the RV septum side wall 414 and mid-septum wall 415 are no longer along or part of the data values for the IM vector 432. In one example, as the lead 422, and consequently the first electrode 428, advance through the mid-septum wall 415, the impedance increases to a maximum when the septal line 418 is reached, and the impedance then begins decreasing. In one example, the impedance when the first electrode 428 is at the proximal portion of the mid-septum wall 415 is 725 Ohms. Between the proximal portion and distal portion of the mid-septum wall 415 the impedance reaches a maximum when the septal line 418 is reached that in one example is 900 Ohms. In the example, when the first electrode reaches the distal portion of the mid-septum wall 415 the impedance is 725 Ohms. In the example, when the first electrode 428 is proximate the LBB and in the LV septum side wall 416 the impedance is in a range between 725-575 Ohms. In another example, the impedance in the RV septum side wall 416 is less than 725 Ohms.

By obtaining impedance data indicative of an impedance along the IM vector with the first electrode located at different depths within the septal wall, the physician can be assisted in advancing the first electrode 428 proximate the LBB without perforating through the LV septum side wall 416 and into a chamber of the heart 400. In one example, the impedance data can include a set of data values associated with different depths of the first electrode within the septal wall. From the set of data values, criteria of interest can be analyzed to determine the location of the first electrode. The criteria of interest can include differences in impedance values, changes in slope of a data value, that may include the impedance, from a positive slope to a negative slope, changes in rate of impedance change, etc.

Figure 4D:
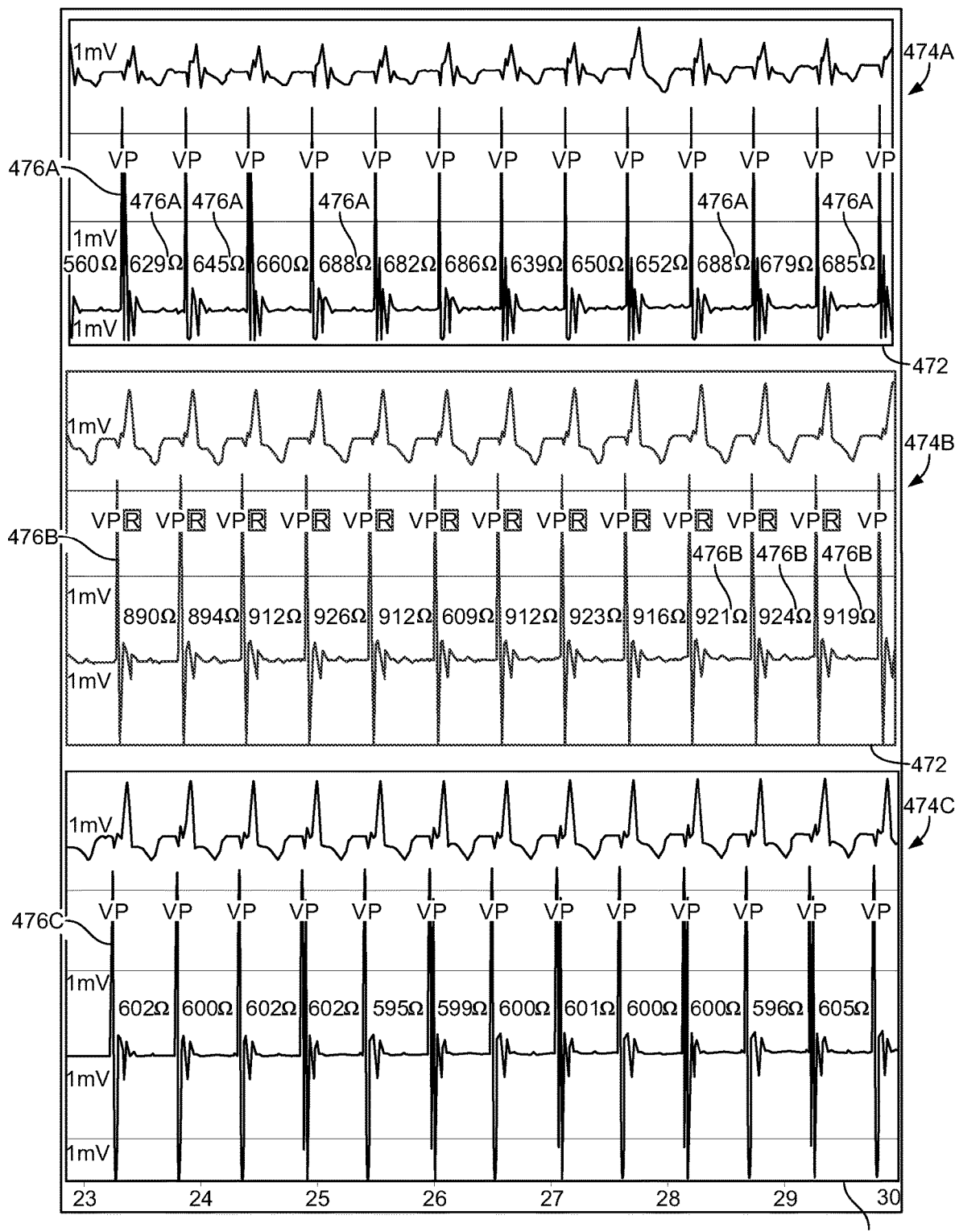
FIG. 4D illustrates a graph of impedance over time, in accordance with embodiments herein.

FIG. 4D illustrates graphs showing impedance as a function of depth over time 472. In particular, the upper graph 474A shows impedance measurements 476A when the first electrode 428 of FIGS. 4A-4C is in the first position as illustrated by FIG. 4A. Meanwhile, the middle graph 474B shows impedance measurements 476B when the first electrode 428 is in the second position as illustrated by FIG. 4B, and the lower graph illustrates impedance measurements 476C when the first electrode 428 is in the third position as illustrated by FIG. 4C. For each graph, an electrocardiograph (ECG) is shown with each signal 476A-C representing a cardiac signal of a patient.

In this manner, the upper graph 474 illustrates impedance data obtained when the first electrode 428 is at the proximal portion of the RV septum side wall and the IM vector 432 includes all of the components, including the septal wall component 434, LV/LA chamber blood component 438, outer heart wall component 440, and the secondary component 442. As illustrated, in this example, the impedance measurements range from 629 Ohms to 688 Ohms. In this manner, each impedance measurement of the impedance data is below 700 Ohms when all components of the medium are within the IM vector 432 between the first electrode 428 and second electrode 430. Meanwhile, when the first electrode 428 advances to the second position in between the proximal portion of the mid-septum wall 415 and the distal portion of the mid-septum wall 415, as illustrated in FIG. 4B, the impedance measurements range between 890 Ohms to 926 Ohms. In this manner each impedance measurement of the impedance data is above 890 Ohms. In this impedance data, the RV septum side wall 414 and part of the mid-septum wall 415 are not in the IM vector 432 between the first electrode 428 and second electrode 430, resulting in an increased impedance. Because of the disparity between the impedance measurements at the first position compared to the impedance measurements at the second position, and specifically, nearly 200 Ohms, the impedance data provides measurement of distance that can facilitate a clinician.

The bottom graph in FIG. 4D shows the first electrode 428 in the third position proximate the LBB. In the third position, both the RV septum side wall 414 and mid-septum wall 415 are not between the first electrode 428 and second electrode 430 within the IM vector 432. As illustrated, the impedance measurements range from 595 Ohms to 605 Ohms. When in the LV septum side wall there is a significant decrease in impedance compared to when the first electrode 428 is at the septal line 418 of the septal wall 402 as illustrated in FIG. 4B. In particular by getting through the mid-septum wall 415, impedance decreases, providing an indicator for a clinician to use signaling that the first electrode is proximate the LBB in the LV septum side wall 416.

Figure 5:
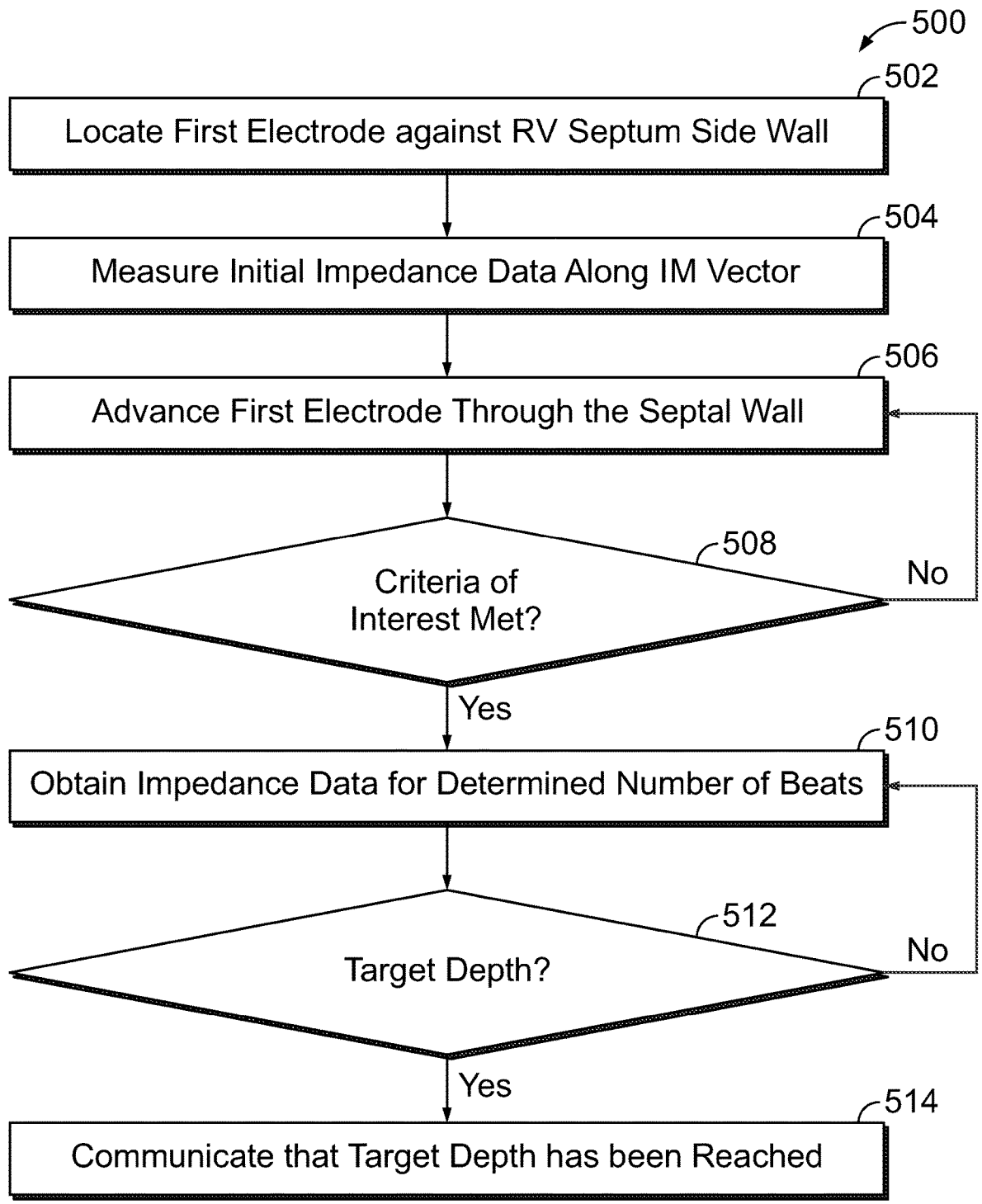
FIG. 5 illustrates a schematic flow block diagram of a process for determining whether an electrode has reached a target depth, in accordance with embodiments herein.

FIG. 5 illustrates a flow block diagram of a process 500 for determining when an electrode has reached a target depth when penetrating a septal wall during implant. In one example, the lead and electrode of FIGS. 4A-4C are utilized for implementing the process. The process can be implemented to implant a lead based device, a leadless device, an IMD, an ICD, an ICM, or the like. Additionally or alternatively, the process of FIG. 5 may be implemented utilizing all or portions of the structural and/or functional aspects of the methods and systems described in copending application Ser. 17/007,696, filed Aug. 31, 2020, and titled "SYSTEMS AND METHODS FOR IMPLANTING A MEDICAL DEVICE USING AN ACTIVE GUIDEWIRE", the complete subject matter of which is expressly incorporated herein by reference in its entirety.

At 502, a first electrode is located against a wall of interest, such as the RV septum side wall of the septal wall, to form an IM vector between the first electrode and a second electrode. The first electrode in one example is on a distal tip of a lead. In another example, the first electrode is on the distal end of a leadless device. In another example, the first electrode is on the distal end of a catheter. The first electrode can be inserted utilizing a catheter. In an example, the second electrode is located on the housing of a subcutaneous device such as an IMD, ICD, ICM, or the like. In another example, the second electrode is not subcutaneous and engages the skin of a patient. The IM vector generally extends along a direct line between the first electrode and second electrode and is configured to measure an impedance between the first electrode and second electrode. The impedance includes all body portions between the first electrode and second electrode resulting in IM vector having different components depending on the medium through which the IM vector travels. In example embodiments the IM vector can include a septal wall component, a LV/LA chamber blood component, an outer heart wall component, and a secondary component. The first electrode in one example is placed in the RV septum side wall proximate the HIS. Optionally, the first electrode is placed in the RV septum side wall between the HIS and the apex of the heart.

At 504, initial impedance data indicative of an impedance along the IM vector is measured. In one example, the one or more processors begin obtaining the impedance data at least by the time the first electrode engages the RV septum side wall. In one example, the impedance is measured in Ohms along the IM vector. When the first electrode first engages the RV septum side wall at a distal end of the RV septum side wall, the IM vector in one example is in a range between 550 Ohms and 650 Ohms.

At 506, the first electrode is advanced though the septal wall in incremental distances to obtain impedance data at different depths within the septal wall as the first electrode is advanced through the septal wall toward the LV septum side wall. In one example, the impedance data includes a set of data values associated with different depths of the first electrode within the septal wall. Optionally, the one or more processors continuously obtain impedance data to provide different sets of data value that can be indicative of the depth of the first electrode within the septal wall. In one example, the first electrode is on the distal tip of a lead that is rotated to facilitate insertion of the first electrode into the septal wall. In another alternative example, the lead and first electrode are pushed through the septal wall without rotation. Still, impedance data, including the data set values, are continuously taken as the first electrode advances through the septal wall. The continuous monitoring of the impedance data during the fixation and tunnelling into the septal wall provides a profile, or data set values, of how far in depth the lead and first electrode are located within the septal wall.

Figure 6:
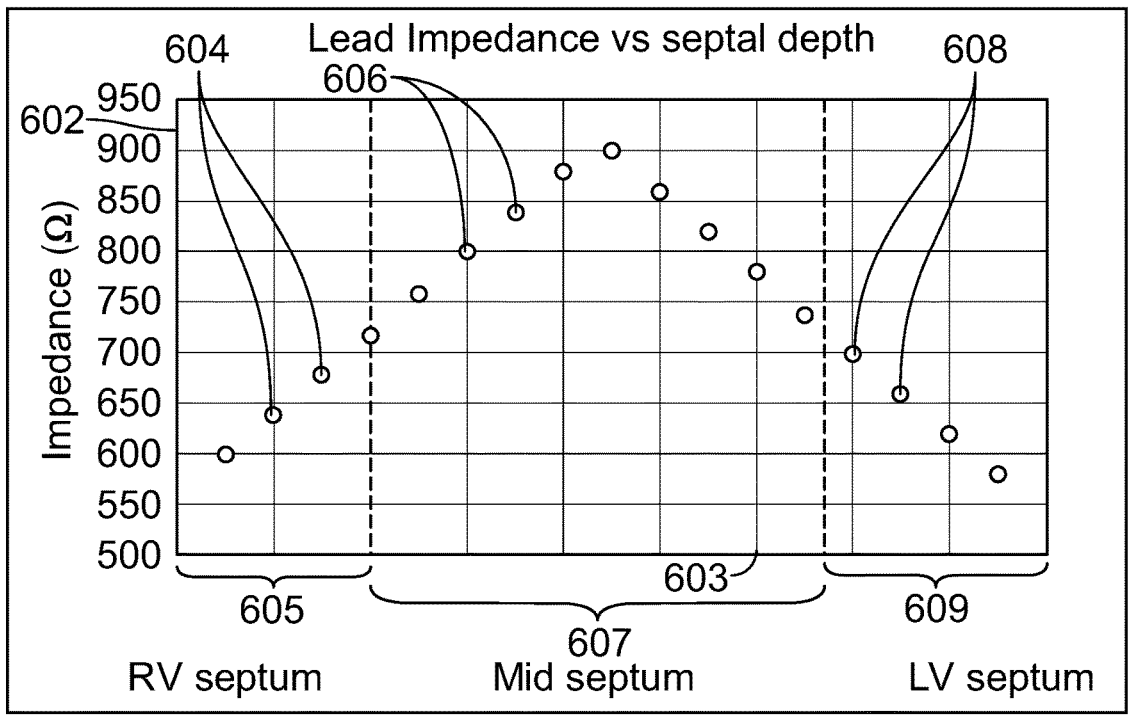
FIG. 6 illustrates a graph of impedance over time, in accordance with embodiments herein.

FIG. 6 illustrates an example graph of impedance data 602, including impedance data with a set of data values associated with different depths 603 of the lead and first electrode into the septal wall. In this example, a first set of data values 604 is indicative of impedances measured when the first electrode is advancing through the RV septum side wall 605, the second set of data values 606 is indicative of impedances measured when the first electrode is advancing through the mid-septum wall 607, and the third set of data values 608 is indicative of impedances measured when the first electrode is proximate the LV septum side wall 609.

Each individual data set value is indicative of an impedance measurement at a given depth. As illustrated, the first set of data values 604 include impedance values that are in a range from 600 Ohms to 725 Ohms, the second set of data values 606 include impedance values that are in a range between 725 Ohms to 900 Ohms, while the third set of data values 608 include impedance values that are in a range between 725 Ohms, and 575 Ohms. In one example, an impedance value may be in both the first set of data values 604 and one of the second set of data values 606 or third set of data values 608. To this end, sets of data values may overlap. Alternatively, the first set of data values 604 may not include a data value from either the second set of data values 606 or the third set of data values 608.

Figure 7:
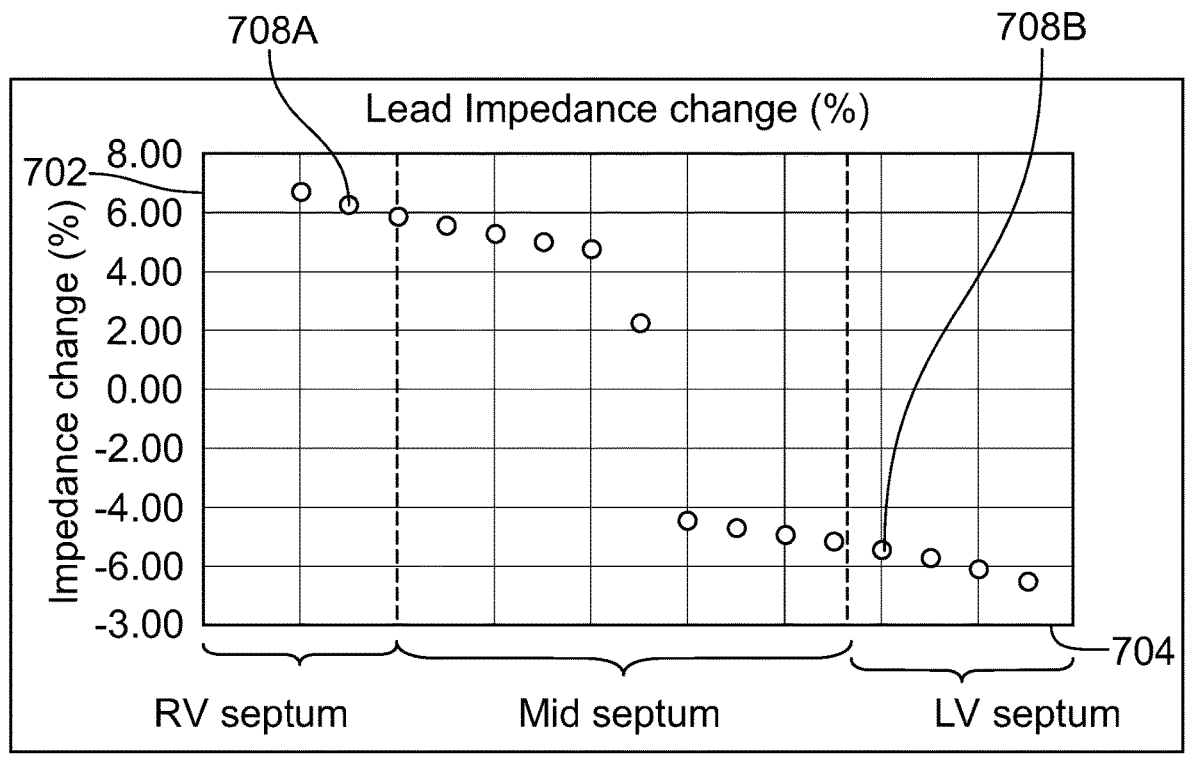
FIG. 7 illustrates a graph of an impedance rate over time, in accordance with embodiments herein.

In addition to sets of data values, criteria of interest may be determined based on the sets of data set values. FIG. 7 illustrates a graph of the change in impedance values 702 at different depths 704 through the septal wall. In this example, a change in impedance 702 between each data set value is calculated to provide the criteria of interest. In one example, the slope of the change in impedance 706 can also be graphed, calculated, determined, etc. for any of the individual data values to provide the criteria of interest. As illustrated, when the first electrode begins advancing through the septal wall, a first data set of values 708A present positive, or increasing impedance changes resulting in a positive slope. However, once the first electrode reaches the septal line of the septal wall, a second data set of values 708B present a decrease in impedance values resulting in a negative slope. As a result, by monitoring the slope of the change in impedance, when the slope turns negative is an indicator that the first electrode has passed the septal line of the mid-septum wall and is approaching the LV septum side wall. In another example, the criteria of interest may include when the impedance data decreases from a first data value to a second data value at a rate greater than a rate threshold percentage. When these types of criteria of interest are satisfied, a surgeon is informed that the first electrode is almost proximate the LBB to prevent perforating through the distal wall of the LV septum side wall into a left chamber of the heart.

With reference back to FIG. 5, at 508, a determination is made whether a criteria of interest has been met. In one example, the criterion of interest is an impedance parameter, a threshold of an impedance parameter, a length of time, a rate threshold, etc. Optionally, the criterion of interest is a threshold Ohm data value such as 725 Ohms where any impedance at or above that Ohm data value is treated as an indication that the first electrode is within the mid-septum wall. In another example, the criterion of interest is the slope of the change in impedance. For example, the slope changing from a positive slope to a negative slope again is an indicator that first electrode is past the septal line of the septal wall. In another example, the criteria of interest can be obtaining an impedance value for a second time, or overlapping impedance values in the same data set value. Again, because the maximum impedance is provided at the septal line, when an impedance value is repeated, an indication of the first electrode advancing past the septal line is provided.

In one example embodiment, the criteria of interest may be an average of a previous number of impedance measurements. In yet another example, a mode, medium, other mathematical relationship, mathematical model, function, algorithm, or the like is utilized to determine the criteria of interest that is associated with and indicates the depth of the first electrode through the septal wall. In yet another example, the criterion of interest is whether the number of Ohms being measured ($\Omega$t) is greater than the Ohms measured at a previous time (e.g. if $\Omega$t>$\Omega$t−1), and/or if the ratio of ($\Omega$t−$\Omega$t−1)/($\Omega$t−1)>0, then the criterion of interest is met.

If at 508, the criterion of interest is met, then the one or more processors obtain impedance data at different depths within the septal wall as the first electrode is advanced through the septal wall. For, example, in an embodiment when the criterion of interest is defined by whether the Ohms at a present time are greater than a previous time ($\Omega$t>$\Omega$t−1), then a maximum number of Ohms has not been reached. As a result, the first electrode has not reached a depth past the septal line, and instead is either still in the RV septum side wall, or is through the RV septum side wall, but not yet to the septal line. Consequently, additional impedance parameters are obtained until a maximum impedance measure is obtained.

If at 508 the criterion of interest is not met, then at 510, the one or more processors continue to obtain impedance measurements for a determined number of beats while the first electrode continues to be advanced through the septal wall. For example, when $\Omega$t>$\Omega$t−1, or when ($\Omega$t−$\Omega$t−1)/($\Omega$t−1)>0, when the slope of the change of impedance changes from positive to negative, etc. an indication is provided that the first electrode has reached the septal line; however, is not proximate the LV septum side wall. As a result, the first electrode continues to be advanced. However, now ohm measurements over a determined number of beats are analyzed to determine when the first electrode is proximate the LV septum side wall.

In one example, the number of beats is one, in another example the number of beats is five, in yet another example the number of beats is ten, etc. In yet another example, the number of beats varies based on either the number of beats, or amount of time required for the first electrode to advance from the proximal side of the RV septum side wall to the septal line. In particular, to avoid perforating through the LV septum side wall, the number of beats, or the amount of time determined, is less than the number of beats, or the amount of time, for the first electrode to advance from the RV septum side wall to the septal line. In this manner, if different surgeons advance a lead with a first electrode at different rates, or if different patients have different heart rates, the differences are accounted for.

At 512, the one or more processors determine when the first electrode is located at a target depth within the septal wall based on the impedance data. In one example, the target depth is a depth where the first electrode is proximate the LBB without perforation through the LV septum side wall. In one example, to determine when the first electrode is located at the target depth, criteria of interest, this time related to the determined number of beats are analyzed. In the embodiment when the maximum impedance measurement is determined, the determined number of beats and corresponding impedance measurement occur after the septal line is reached, and when impedance measurements are decreasing.

In one example, the criterion of interest is the percent change in impedance from an initial impedance value, and when the percent change in impedance meets or exceeds a threshold rate percentage, the criterion of interest is met. In the example, the change in impedance threshold is considered a rate threshold, and the percentage is the rate threshold percentage. In another example, the impedance in Ohms at a time ($\Omega$t) after the maximum impedance is obtained is subtracted from the maximum impedance value (e.g. an initial impedance value ($\Omega$i)) and then divided by the maximum impedance value and multiplied by 100% (e.g. ($\Omega$t−$\Omega$i)/($\Omega$i)*100%). If the rate threshold percentage is not reached, a next impedance value ($\Omega$t) is measured and the previously measured impedance value becomes the initial impedance value ($\Omega$i), and the percentage is again determined to see if the threshold percentage has been reached. As a result, the percent of impedance drop is determined until the threshold rate percentage is reached. As a result of advancing past the mid-septum wall and proximate the LBB, an increased impedance value drop is provided, causing a larger rate decrease in the change impedance value as compared to the rate drop when both impedance value are obtained when the first electrode is still in the mid-septum wall and is not proximate the LBB. In one example, the threshold rate percentage is 10%. The determined percentage is determined based on the percent decline in impedance value required to be indicative the first electrode is no longer in the mid-septum wall and is proximate the LBB.

In another example, the criterion of interest is an impedance value drop from the maximum impedance value ($\Omega$ max). Optionally, once the maximum impedance value ($\Omega$ max) is determined, the impedance value for each beat of the series of beats after the maximum impedance value is determined is obtained and subtracted from the maximum impedance value to determine if the impedance value has dropped below a threshold amount (e.g. $\Omega$ max−$\Omega$t=/>determined threshold). In one example, the determined threshold is 1000. In particular, the maximum impedance value for a give patient is determined, including based on historical data and information. In one example, a patient is similarly situated to the patient that provided the data set values presented in the graph of FIG. 4 where the maximum impedance value is approximately 900$\Omega$ and the determined threshold is 250$\Omega$t. In particular, the range of the impedance values when the first electrode is in the mid-septum wall is between 725 Ohms and 900 Ohms, therefore, any determined maximum will be approximately 900 Ohms. Meanwhile, the range of impedance values for when the first electrode is proximate the LBB is between 725 Ohms, and 575 Ohms. A determined threshold being 250 Ohms thus indicates being 250 Ohms below 900 Ohms, or approximately 650 Ohms. Such a determined threshold ensures that if the maximum impedance value is slightly incorrect as a result of timing of the reading, the determined threshold still results in the first electrode being proximate the LBB without perforating through the distal end of the LV septum side wall into a left chamber of the heart.

In yet another example, the percentage of impedance value drop is the criteria of interest utilized to determine if the first electrode has advanced into the LV septum side wall. In this example, similar to the previous example, a measured impedance value at a given time (e.g. $\Omega$t) after the maximum impedance value is determined is calculated and then dived by the maximum impedance value and multiplied by 100% (e.g. ($\Omega$ max−$\Omega$t)/$\Omega$ max*100%). In this manner, a percent decline from the maximum impedance value is utilized to determine that the first electrode has advanced proximate the LBB. By utilizing a threshold percentage, instead of determining that a first patient is similarly situated to a second patient, variances in maximum impedances across different patients are accounted for to prevent not advancing the first electrode proximate the LBB or advancing the first electrode through the LV septum side wall. In one example the threshold percentage may be 10%, whereas in another example the threshold percentage may be 25%, and in yet another example the threshold percentage is less than 10% or greater than 25%.

In another example, the criteria of interest can be a percentage of the change of impedance value between two impedance value measurements obtained after the maximum impedance value is determined. In the example, a previous impedance value $\Omega t-1$ is subtracted from a current impedance value $\Omega t$ and divided by the previous impedance value and multiplied by 100% (e.g. ($\Omega t-1-\Omega t$)/$\Omega t-1$*100%. This value is then compared to a rate threshold percentage. In one example the rate threshold percentage can be −2%, −5%, −10% etc. Because a decrease in impedance occurs when the first electrode advances through the distal portion of the mid-septum wall and the LV septum side wall, a large drop in the rate threshold percentage is provided such that the threshold percentage identifies the drop. In this manner, a determination can be made that the first electrode has advanced proximate the LBB.

In each example embodiment, the one or more processors analyze the impedance data, including sets of data values associated with different depths of the first electrode within the septal wall. The sets of data values can include two consecutive impedance values, the maximum impedance value, non-consecutive impedance values, etc. Then based on the analysis, a determination is made whether a target depth has been reached. To make the determination, comparisons to impedance thresholds, comparisons to percentage thresholds, comparisons to previous impedance values of other patients, a combination of any of these, a calculation utilizing an algorithm based on one or more of the comparisons, a model based one or more of the comparisons, or the like are utilized.

If at 512 the one or more processors determine the first electrode is not located at a target depth within the septal wall based on the impedance data, the one or more processors continue to obtain impedance measurements for a determined number of beats while the first electrode continues to be advanced through the septal wall. In an example embodiment, the one or more processors continue obtaining data and adding to at least one set of data values to update calculations, determinations, etc. to identify the target depth has been reached.

If at 512 the one or more processors determine the first electrode is located at the target depth within the septal wall based on the impedance data, then at 514, the one or more processors communicate that the target depth has been reached. In one example, to communicate that the depth has been reached a change in color on a display screen, an audible sound, statement, binging, etc., a haptic response such as a vibration, a written phrase on a display screen, etc. is provided In another example embodiment where a robotic arm or device is being utilized to facilitate insertion, the robotic arm may deactivate. In each instance, a manner of communicating that the target depth has been reached is presented, assisting the surgeon in placement of the first electrode proximate the LBB without perforating the distal portion of the LV septum side wall. Consequently, the implanting of the medical device is improved by providing more accuracy and safety.

Figure 8:
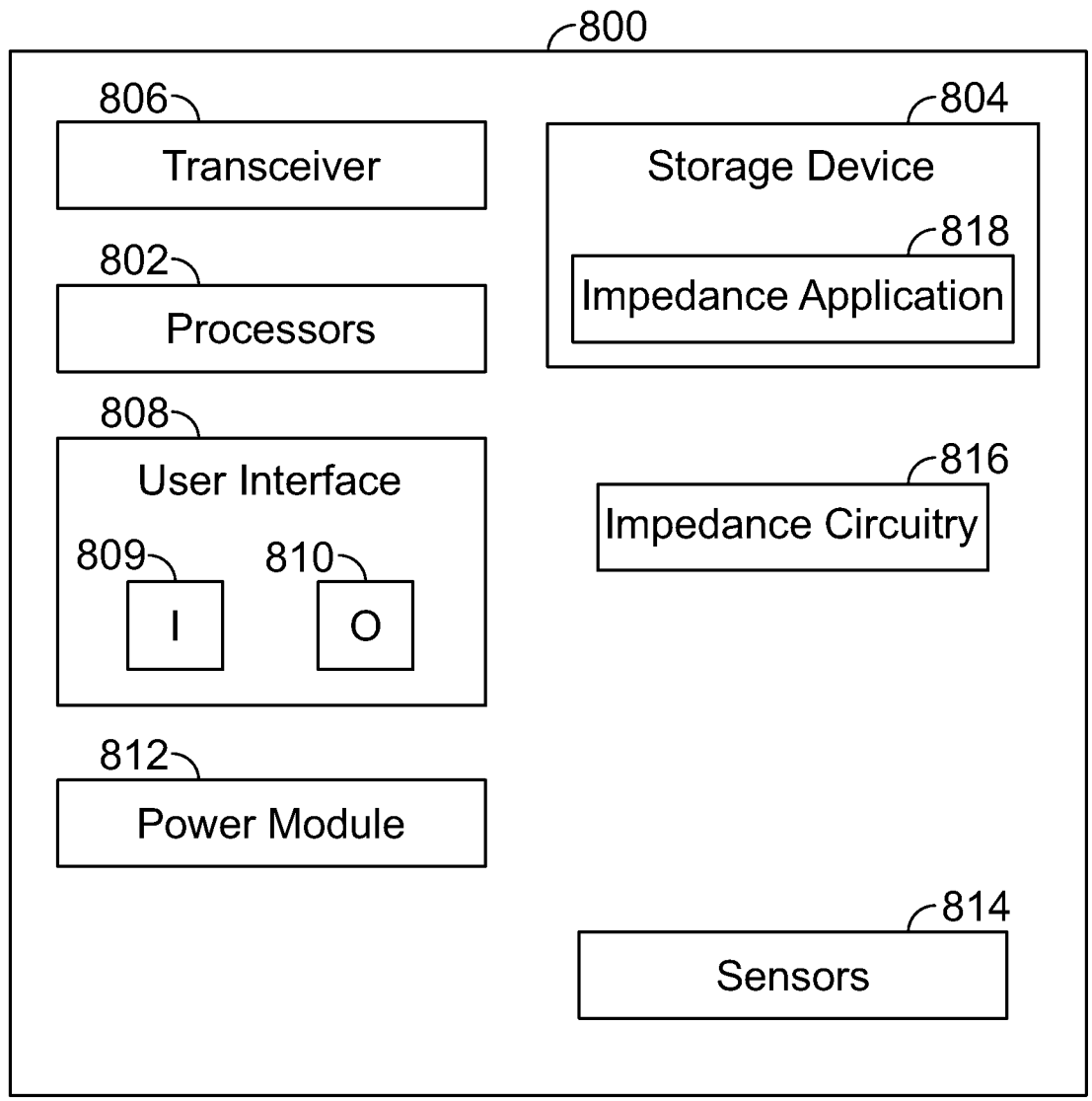
FIG. 8 illustrates a schematic block diagram of an external device, in accordance with embodiments herein.

FIG. 8 illustrates a simplified block diagram of an external device 600. In one example, the external device 800 can be the external device 104 of FIG. 1, external device 204 of FIG. 2, an external device utilized in association with another IMD, including the leadless IMD of FIG. 3, or the like.

The external device 800 includes components such as one or more processors 802 (e.g., a microprocessor, microcomputer, application-specific integrated circuit, etc.), one or more local storage medium (also referred to as a memory portion) 804, one or more transceivers 806, a user interface 808 which includes one or more input devices 809 and one or more output devices 810, a power module 812, one or more sensors 814, and impedance circuit 816. All of these components can be operatively coupled to one another, and can be in communication with one another, by way of one or more internal communication links, such as an internal bus.

The local storage medium 804 can encompass one or more memory devices of any of a variety of forms (e.g., read only memory, random access memory, static random access memory, dynamic random access memory, etc.) and can be used by the processor 802 to store and retrieve data. The data that is stored by the local storage medium 804 can include, but not be limited to, CA signals, acceleration signals, impedance data, sets of data values, algorithms, applications, or the like. The local storage medium 804 can also include executable code that controls basic functions of the external device 800, such as interaction among the various components, communication with IMDs via the transceiver 806 and storage and retrieval of applications and context data to and from the local storage medium 804. The transceiver 806 may provide wire communication, wireless communication, cellular communication, over the air communication, network communication, electronic communication, a combination thereof, or the like.

In one example embodiment, the local storage medium includes an impedance application 818. The impedance application 818 obtains and determines impedance data over time. In one example, the impedance application 818 receives signals from the impedance circuit 816 related to the impedance between a first electrode and a second electrode. This impedance data includes changes in the impedance as the first electrode advances through a wall of the heart. Optionally, the wall can be the septal wall of the heart. The impedance application 818 can make determinations about the location of the first electrode based on the impedance data, and/or based on sets of data values related to the impedance data. The determinations include a determination related to whether the first electrode has reached a target depth. Based on the determined location of the first electrode, the impedance application 818 can also have the transceiver 806 communicate a message to a physician. The communication can include a message displayed on the output device 810, an auditory sound, message, etc., an electronic message communicated to another device, a haptic response, or the like.

The input and output devices 809, 810 may each include a variety of visual, audio, and/or mechanical devices. For example, the input devices 809 can include a mechanical input device such as a keyboard, keypad, selection hard and/or soft buttons, switch, touchpad, touch screen, icons on a touch screen, a touch sensitive areas on a touch sensitive screen and/or any combination thereof. The output devices 810 can include a visual output device such as a liquid crystal display screen, a mechanical output device such as a vibrating mechanism, etc. The display may be touch sensitive to various types of touch and gestures. As further examples, the output device(s) 810 may include a touch sensitive screen, a non-touch sensitive screen, a text-only display, and/or any combination thereof.

The user interface 808 permits the user to select one or more of a switch, button, or icon to collect user characteristics, and/or electronic device characteristics. The user interface 808 can also direct the one or more sensors 814 or impedance circuit 816 to obtain CA signals, impedance data, posture data, etc. Because the user interface 808 may be utilized to obtain the CA signals, impedance data, posture data, etc. a physician can utilize the user interface 808 to determine the location of a first electrode in a heart wall, including to determine whether a target depth has been reached.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network, and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving, and accessing structured or unstructured data. Database servers may include table-based servers, document-based servers, unstructured servers, relational servers, non-relational servers, or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer, or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A system, comprising:
   a first electrode configured to be located within a septal wall;
   a second electrode configured to be located outside of the septal wall;
   an impedance circuit configured to measure impedance along an impedance monitoring (IM) vector between the first and second electrodes;
   a memory configured to store program instructions;
   one or more processors that, when executing the program instructions, are configured to:
      obtain impedance data indicative of an impedance along the IM vector with the first electrode located at different depths within the septal wall as the first electrode advances through the septal wall, the impedance data including a set of data values associated with the different depths of the first electrode within the septal wall as the first electrode advances through the septal wall;
      determine when the first electrode is located at a target depth within the septal wall based on the impedance data; and
      communicate an alert indicative of the target depth for the first electrode.

2. The system of claim 1, wherein the target depth locates the first electrode proximate to the left bundle branch (LBB).

3. The system of claim 1, wherein the one or more processors are configured to determine that the first electrode is located proximate the LBB when the impedance data decreases from a first data value above a threshold to a second data value below the threshold.

4. The system of claim 1, wherein the one or more processors are configured to determine that the first electrode is located proximate the LBB based at least in part on a slope of the data value changes from positive to negative.

5. The system of claim 1, wherein the one or more processors are configured to determine that the first electrode is located proximate the LBB when the impedance data decreases from a first data value to a second data value at a rate greater than a rate threshold percentage.

6. The system of claim 1, wherein the determine operation includes determining when the data values satisfy a criteria of interest.

7. The system of claim 1, wherein the determine operation further comprises comparing the data values, within the set of data values, to one another to determine a relation; and determining when the relation satisfies the criteria of interest.

8. The system of claim 1, wherein the criteria of interest is at least one of change in impedance value, a slope value, a change in impedance rate value, a change in impedance percentage, or a change in impedance rate percentage.

9. The system of claim 1, wherein the target depth includes a point where the first electrode is proximate the LBB and does not perforate a LV septum side wall distal wall of the septal wall.

10. The system of claim 1, further comprising a leadless IMD having the first electrode.

11. The system of claim 1, wherein the impedance data includes a septal wall component, a left ventricle or left atrial (LV/LA) chamber blood component, an outer heart wall component, and a secondary component for a region outside of the heart wall.

12. The system of claim 1, wherein the first electrode and the second electrode are configured to measure the impedance data, the first electrode provided proximate a distal tip of a lead located in the right ventricle RV, the second electrode located remote from the RV.

13. The system of claim 12, wherein the second electrode is located on a housing of an implantable pulse generator, or in one of the right atrium, right ventricle, left ventricle, or left atrium.

14. A computer implemented method, wherein under control of one or more processors configured with specific executable instructions, the method comprises:

obtaining impedance data indicative of an impedance along an impedance monitoring (IM) vector with a first electrode located at different depths within a septal wall as the first electrode advances through the septal wall, the impedance data including a set of data values associated with the different depths of the first electrode within the septal wall as the first electrode advances through the septal wall; and determining when the first electrode is located at a target depth within the septal wall based on the impedance data; and communicating an alert indicative of the target depth for the first electrode.

15. The method of claim 14 further comprising:
determining that the first electrode is located proximate the LBB when the impedance data decreases from a first data value above a threshold to a second data value below the threshold.

16. The method of claim 14, further comprising determining that the first electrode is located proximate the LBB based at least in part on a slope of the data values changing from positive to negative.

17. The method of claim 14, wherein the determining operation includes determining when the data values satisfy a criteria of interest.

18. The method of claim 14, wherein the determining operation further comprises comparing the data values, within the set of data values, to one another to determine a relation; and determining when the relation satisfies the criteria of interest.

19. The method of claim 14, wherein obtaining the impedance data comprises measuring the impedance data with the first electrode and the second electrode, the first electrode provided proximate a distal tip of a lead located in the right ventricle RV, the second electrode located remote from the RV.

20. The method of claim 14, further comprising determining that the first electrode is located proximate the LBB when the impedance data decreases from a first data value to a second data value at a rate greater than a rate threshold percentage.

* * * * *